United States Patent
Ou Yang et al.

(10) Patent No.: US 11,872,339 B2
(45) Date of Patent: Jan. 16, 2024

(54) NASAL MUCUS SUCTION DEVICE AND CHANNEL FORMING METHOD THEREOF

(71) Applicant: AViTA Corporation, New Taipei (TW)

(72) Inventors: Hsing Ou Yang, New Taipei (TW); Jui-Yang Huang, New Taipei (TW); Ching-Chin Hsiao, New Taipei (TW)

(73) Assignee: AVITA CORPORATION, New Taipei (TW)

( * ) Notice: Subject to any disclaimer, the term of this patent is extended or adjusted under 35 U.S.C. 154(b) by 0 days.

(21) Appl. No.: 17/691,132

(22) Filed: Mar. 10, 2022

(65) Prior Publication Data

US 2022/0296800 A1 Sep. 22, 2022

(30) Foreign Application Priority Data

Mar. 17, 2021 (TW) ................................. 110109604

(51) Int. Cl.
*A61M 1/00* (2006.01)
(52) U.S. Cl.
CPC ................ *A61M 1/64* (2021.05); *A61M 1/87* (2021.05); *A61M 2202/04* (2013.01); *A61M 2205/42* (2013.01); *A61M 2207/00* (2013.01); *A61M 2210/0618* (2013.01)
(58) Field of Classification Search
CPC .. A61M 2210/0618; A61M 1/65; A61M 1/60; A61M 1/0003; A61M 1/80; A61M 1/74; A61M 1/78; A61M 1/64; A61M 1/87; A61M 2205/42; A61M 2202/04; A61M 2207/00; A61H 35/04; A61H 2205/023
See application file for complete search history.

(56) References Cited

U.S. PATENT DOCUMENTS

| 6,471,679 | B1 * | 10/2002 | Suh | A61M 1/78 604/319 |
|---|---|---|---|---|
| 11,524,105 | B1 * | 12/2022 | Chen | A61M 1/73 |
| 2009/0048581 | A1 * | 2/2009 | Sebban | A61M 1/65 604/319 |

(Continued)

FOREIGN PATENT DOCUMENTS

| CN | 104258480 | 1/2015 |
|---|---|---|
| CN | 107638600 | 1/2018 |

(Continued)

*Primary Examiner* — Erich G Herbermann
*Assistant Examiner* — Linnae E. Raymond
(74) *Attorney, Agent, or Firm* — Che-Yang Chen; Law Office of Michael Chen

(57) ABSTRACT

A nasal mucus suction device includes an air pump and a head structure. The air pump has an intake tube and an outlet tube. The head structure is coupled to the intake tube and the outlet tube of the air pump, and defines a channel between a nasal mucus suction inlet and a gas outlet. The channel includes a first channel section in communication with the nasal mucus suction inlet, and a second channel section in communication with the gas outlet. The first channel section includes at least one mucus storage cavity, the second channel section is in communication with the intake tube and the outlet tube of the air pump. The first channel section has a maximized path length, and includes an anti-backflow channel structure. The second channel section includes a noise reduction space.

13 Claims, 5 Drawing Sheets

(56) References Cited

U.S. PATENT DOCUMENTS

2020/0306425 A1\* 10/2020 Zhang .................... A61B 17/24
2022/0143294 A1\* 5/2022 Wei ........................ A61M 1/64

FOREIGN PATENT DOCUMENTS

| CN | 109152869 | | 1/2019 | | |
|----|-----------|---|--------|---|---|
| CN | 110478541 | A \* | 11/2019 | .......... | A61M 1/0001 |
| CN | 209645510 | | 11/2019 | | |
| CN | 209645510 | U \* | 11/2019 | .......... | A61M 1/0023 |
| CN | 210056896 | | 2/2020 | | |
| CN | 210078400 | | 2/2020 | | |
| CN | 210992129 | | 7/2020 | | |
| CN | 211214603 | | 8/2020 | | |
| CN | 212141025 | | 12/2020 | | |
| FR | 2912062 | A1 \* | 8/2008 | .......... | A61M 1/0001 |
| JP | 6517566 | B2 \* | 5/2019 | .......... | A61M 1/0001 |
| KR | 20090011745 | | 2/2009 | | |
| TW | M261218 | U | 4/2005 | | |
| TW | M544939 | | 7/2017 | | |

\* cited by examiner

NASAL MUCUS SUCTION DEVICE AND
CHANNEL FORMING METHOD THEREOF

BACKGROUND OF THE PRESENT
INVENTION

Field of Invention

The present invention relates to a nasal mucus suction device. More particularly, the present invention relates to a nasal mucus suction device capable of preventing backflow of nasal mucus and reducing noise, and a channel forming method thereof.

Description of Related Arts

Nasal cleaning and medical care are very important clinically, so products with nasal mucus suction functions are developed for cleaning or medical use. Especially in home care, it is necessary to provide simple and quick nasal care including a function of sucking of patient's nasal mucus or phlegm.

According to the conventional technology, the nasal mucus suction device uses an air pump as a power source to generate suction, but unnecessary noise is often caused by the air pump during the operation of the nasal mucus suction device. In addition, in order to prevent the stored nasal mucus from overflowing, the conventional nasal mucus suction device must have a limitation in a holding angle; however, when the user operates the conventional nasal mucus suction device and rotates the holding angle of the conventional nasal mucus suction device, nasal mucus easily overflows an outer shell of the conventional nasal mucus suction device.

Therefore, the present invention provides a nasal mucus suction device having a channel for preventing backflow of nasal mucus and reducing noise, and a channel forming method thereof, so as to improve practicability in the industry.

SUMMARY OF THE PRESENT INVENTION

An objective of the present invention is to disclose a nasal mucus suction device and a channel forming method, and provide a structure formed in a nasal mucus suction channel to prevent backflow and overflow of nasal mucus. Another objective of the present invention is to disclose a nasal mucus suction device and a channel forming method thereof, to provide a noise reduction structure formed in an outlet channel to reduce noise caused by operation of an air pump.

In order to achieve the objective, the present invention provides a nasal mucus suction device including an air pump and a head structure. The air pump includes an intake tube and an outlet tube. The head structure is coupled to the intake tube and the outlet tube of the air pump, wherein the head structure defines a channel between a nasal mucus suction inlet and a gas outlet, the channel includes a first channel section in communication with the nasal mucus suction inlet, and a second channel section in communication with the gas outlet, the first channel section includes at least one mucus storage cavity, and the second channel section in communication with the intake tube and the outlet tube of the air pump. The first channel section includes an air channel and a nasal mucus channel, the second section is extended from the air channel to the gas outlet. A path length of the first channel section is maximized, and the first channel section comprises an anti-backflow channel structure. The second channel section includes a noise reduction space in communication with the outlet tube of the air pump.

According to an embodiment of the present invention, the first channel section of the head structure includes a front cover, an inner cup and an outer cup. The front cover includes the nasal mucus suction inlet. The inner cup includes the first mucus storage cavity in communication with the nasal mucus suction inlet. The outer cup includes the second mucus storage cavity in communication with the intake tube of the air pump, wherein the second mucus storage cavity accommodates at least one part of the inner cup, so that nasal mucus overflowing from the first mucus storage cavity is accommodated in the second mucus storage cavity. The first channel section further includes a cup cover having a flow guidance tube, the cup cover is coupled to between the front cover and the cup lid, so that the guidance tube passes through the opening of the cup lid, the flow guidance tube guides nasal mucus from the nasal mucus suction inlet to flow into the first mucus storage cavity. The outer cup includes a middle tube formed on a bottom thereof, the middle tube is in communication with the intake tube of the air pump and the second mucus storage cavity, and an inner channel length of the middle tube is greater than a bottom thickness of the outer cup. The outer cup includes a lower ring wall extended from a bottom of the inner side thereof and surrounding the middle tube, and the inner cup includes an upper ring wall extended from a bottom of the outer side thereof and surrounding a lower ring wall of the outer cup, the upper ring wall and the lower ring wall form a plurality of curved paths of the first channel section inside the second mucus storage cavity, so that the path length of the first channel section is maximized.

According to an embodiment of the present invention, the second channel section of the head structure includes a connection block, the connection block includes an intake channel and an outlet channel, the intake channel is in communication with the second mucus storage cavity of the outer cup and the intake tube of the air pump, and the outlet channel is in communication with the outlet tube and the gas outlet of the air pump. The first channel section includes a cup lid having an opening, and the cup lid covers a cup edge of the inner cup.

In order to achieve the objective, the present invention provides a channel forming method for a nasal mucus suction device, the nasal mucus suction device includes an air pump and a head structure, and the air pump includes an intake tube and an outlet tube, and the head structure defines a channel between a nasal mucus suction inlet and a gas outlet, the channel comprises a first channel section in communication with the nasal mucus suction inlet, and a second channel section in communication with the gas outlet, and the channel forming method includes steps of: maximizing a path length of the first channel section, and forming an anti-backflow channel structure in the first channel section; disposing at least one mucus storage cavity in the first channel section; disposing a noise reduction space in the second channel section and in communication with the outlet tube of the air pump.

According to an embodiment of the present invention, the channel forming method of the present invention further includes steps of: disposing a front cover in the first channel section, wherein the front cover includes a nasal mucus suction inlet; disposing an inner cup in the first channel section, wherein the inner cup includes a first mucus storage cavity in communication with the nasal mucus suction inlet; disposing an outer cup in the first channel section, wherein the outer cup includes a second mucus storage cavity in communication with the intake tube of the air pump and configured to accommodate at least one part of the inner cup, so that the nasal mucus overflowing from the first mucus storage cavity is accommodated in the second mucus storage cavity.

According to an embodiment of the present invention, the channel forming method further includes a step of forming a plurality of curved paths of the first channel section in the second mucus storage cavity between an outer side bottom of the inner cup and an inner side bottom of the outer cup, to maximize a path length of the first channel section.

According to an embodiment of the present invention, the channel forming method further includes steps of: disposing a base in the second channel section to define the noise reduction space in communication with the gas outlet; disposing a connection block in the second channel section, wherein the connection block includes an intake channel and an outlet channel, and the intake channel is in communication with the first channel section and the intake tube of the air pump, and the outlet channel is in communication with the outlet tube and the gas outlet of the air pump.

Therefore, the nasal mucus suction device and the channel forming method of the present invention can prevent nasal mucus from easily overflowing when a user holds the nasal mucus suction device and rotate a holding angle, and the noise reduction structure in the channel can effectively reduce the noise caused by the air pump when the device of the present invention is in operation.

BRIEF DESCRIPTION OF THE DRAWINGS

The structure, operating principle and effects of the present invention will be described in detail by way of various embodiments which are illustrated in the accompanying drawings.

FIG. 2 is a sectional view of a head structure coupled to an air pump of a nasal mucus suction device of the present invention, wherein FIG. 2 is taken along a section line BB of FIG. 5.

FIG. 3 is a sectional view of a head structure of a nasal mucus suction device of the present invention, wherein FIG. 3 is taken along section line AA of FIG. 5.

DETAILED DESCRIPTION OF THE PREFERRED EMBODIMENT

Figure 1:
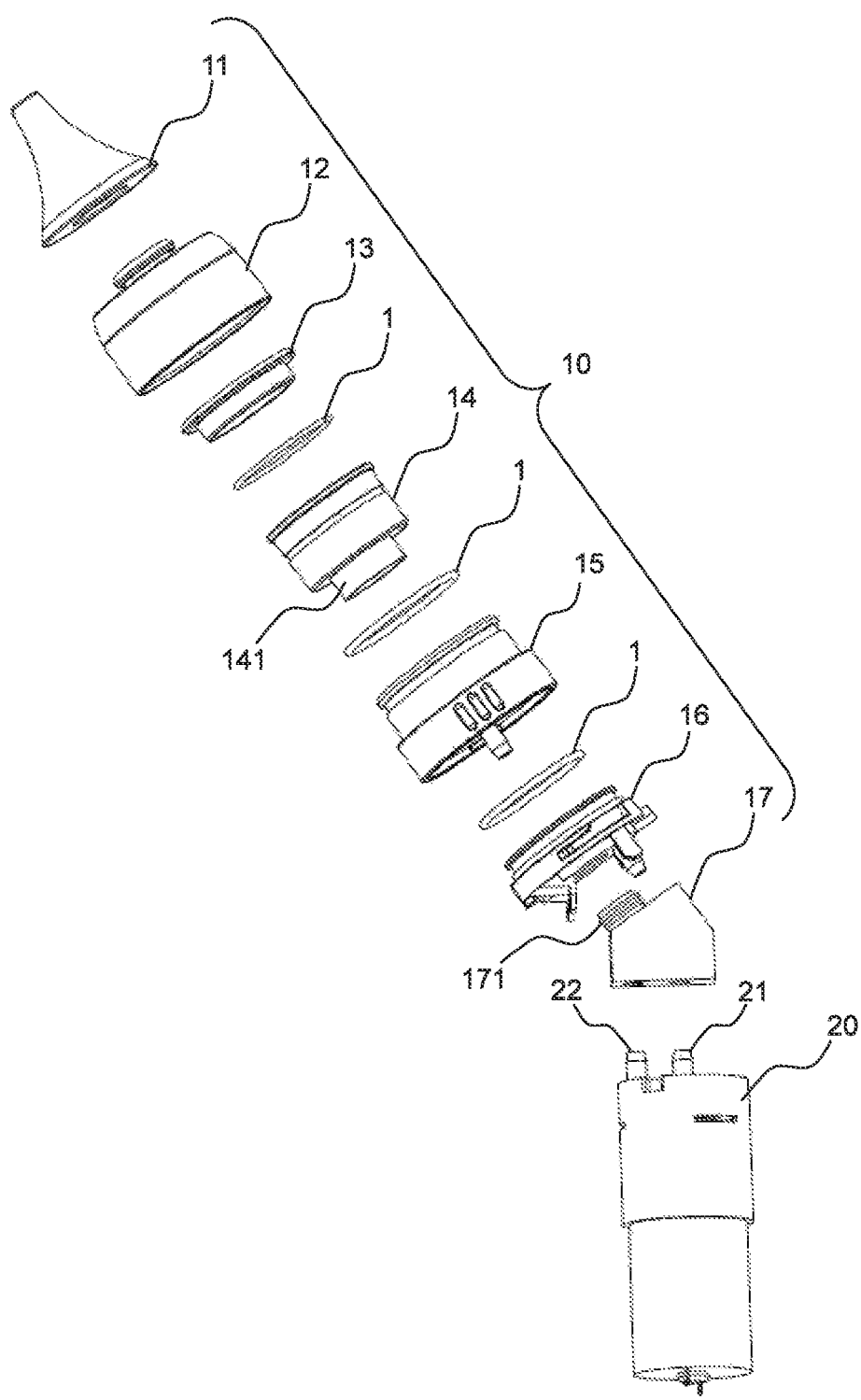
FIG. 1 is an exploded view of a nasal mucus suction device of the present invention.

The following embodiments of the present invention are herein described in detail with reference to the accompanying drawings. These drawings show specific examples of the embodiments of the present invention. These embodiments are provided so that this disclosure will be thorough and complete, and will fully convey the scope of the invention to those skilled in the art. It is to be acknowledged that these embodiments are exemplary implementations and are not to be construed as limiting the scope of the present invention in any way. Further modifications to the disclosed embodiments, as well as other embodiments, are also included within the scope of the appended claims.

These embodiments are provided so that this disclosure is thorough and complete, and fully conveys the inventive concept to those skilled in the art. Regarding the drawings, the relative proportions and ratios of elements in the drawings may be exaggerated or diminished in size for the sake of clarity and convenience. Such arbitrary proportions are only illustrative and not limiting in any way. The same reference numbers are used in the drawings and description to refer to the same or like parts. As used herein, the singular forms "a", "an" and "the" are intended to include the plural forms as well, unless the context clearly indicates otherwise.

It is to be acknowledged that, although the terms 'first', 'second', 'third', and so on, may be used herein to describe various elements, these elements should not be limited by these terms. These terms are used only for the purpose of distinguishing one component from another component. Thus, a first element discussed herein could be termed a second element without altering the description of the present disclosure. As used herein, the term "or" includes any and all combinations of one or more of the associated listed items.

It will be acknowledged that when an element or layer is referred to as being "on," "connected to" or "coupled to" another element or layer, it can be directly on, connected or coupled to the other element or layer, or intervening elements or layers may be present. In contrast, when an element is referred to as being "directly on," "directly connected to" or "directly coupled to" another element or layer, there are no intervening elements or layers present.

In addition, unless explicitly described to the contrary, the words "comprise" and "include", and variations such as "comprises", "comprising", "includes", or "including", will be acknowledged to imply the inclusion of stated elements but not the exclusion of any other elements.

Figure 2:
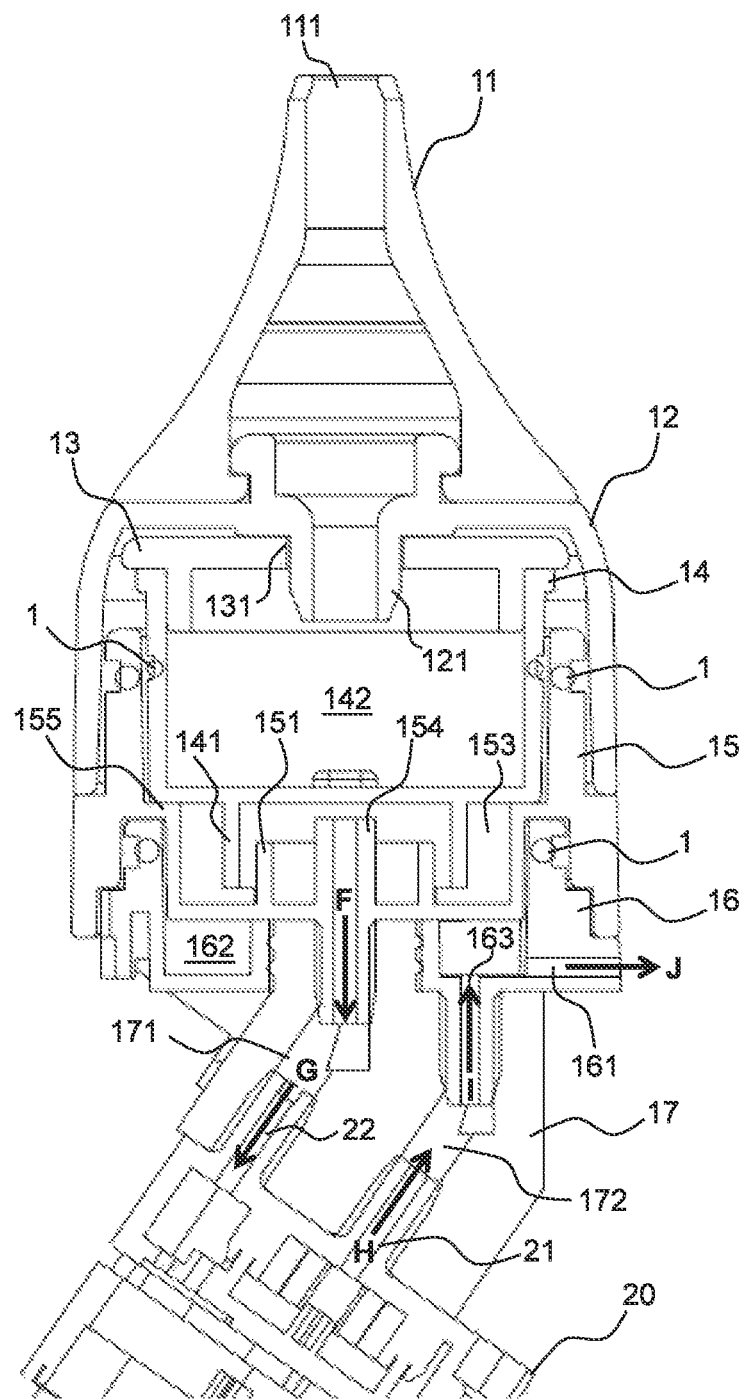

Please refer to FIG. 1, which shows an exploded view of a nasal mucus suction device of the present invention. In an embodiment of the present invention, a nasal mucus suction device includes a head structure 10 and an air pump 20, and the air pump 20 includes an intake tube 22 and an outlet tube 21. The head structure 10 is coupled to the intake tube 22 and the outlet tube 21 of the air pump 20. As shown in FIG. 1, the head structure 10 is formed by a front cover 11, a cup cover 12, a cup lid 13, an inner cup 14, an outer cup 15, a base 16 and a connection block 17; the inner cup 14 includes a first mucus storage cavity 142, and the outer cup 15 includes a second mucus storage cavity 153. As shown in FIG. 2, an O-shaped ring 1 is disposed between an outer side of the inner cup 14 and an inner side of the outer cup 15, to restrict the flowing path for the nasal mucus overflowing the first mucus storage cavity 142; that is, the O-shaped ring 1 disposed between the outer side of the outer cup 15 and the inner side of the cup cover 12 prevents the nasal mucus overflowing the first mucus storage cavity 142 from flowing outside the cup cover 12.

Figure 5:
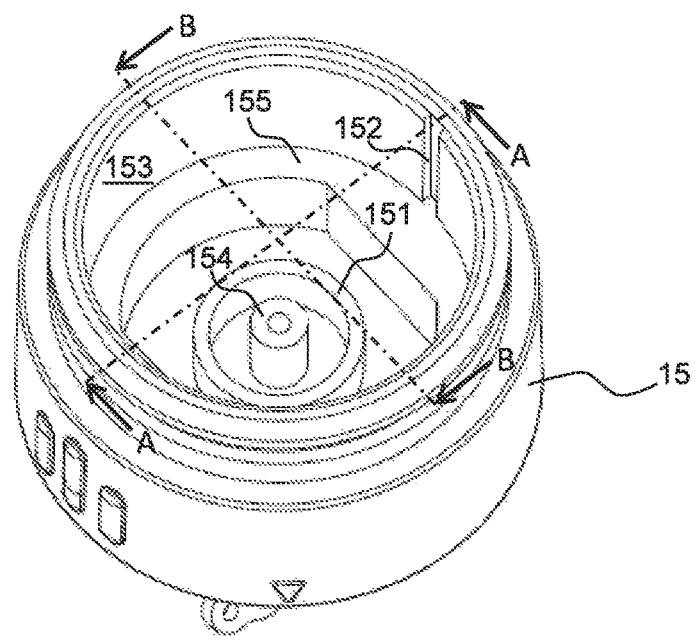
FIG. 5 is a perspective view of an outer cup of a nasal mucus suction device of the present invention.

Please refer to FIG. 2, which shows a sectional view of a head structure of a coupled to the air pump 20, according to a nasal mucus suction device of the present invention, and FIG. 2 is taken along a section line BB of FIG. 5. In an embodiment, the front cover 11 includes a nasal mucus suction inlet 111, the base 16 includes a gas outlet 161. The head structure 10 defines a channel between a nasal mucus suction inlet 111 and a gas outlet 161. The channel includes a first channel section in communication with the nasal mucus suction inlet 111, and a second channel section in communication with the gas outlet 161; the first channel section serves as a common channel for an air channel and the nasal mucus channel and include paths A, B, C, D and E, as shown in FIG. 3; the second channel section is extended from the air channel of the first channel section to the gas outlet 161, and includes paths F, G, H, I and J, as shown in FIG. 2.

Figure 3:
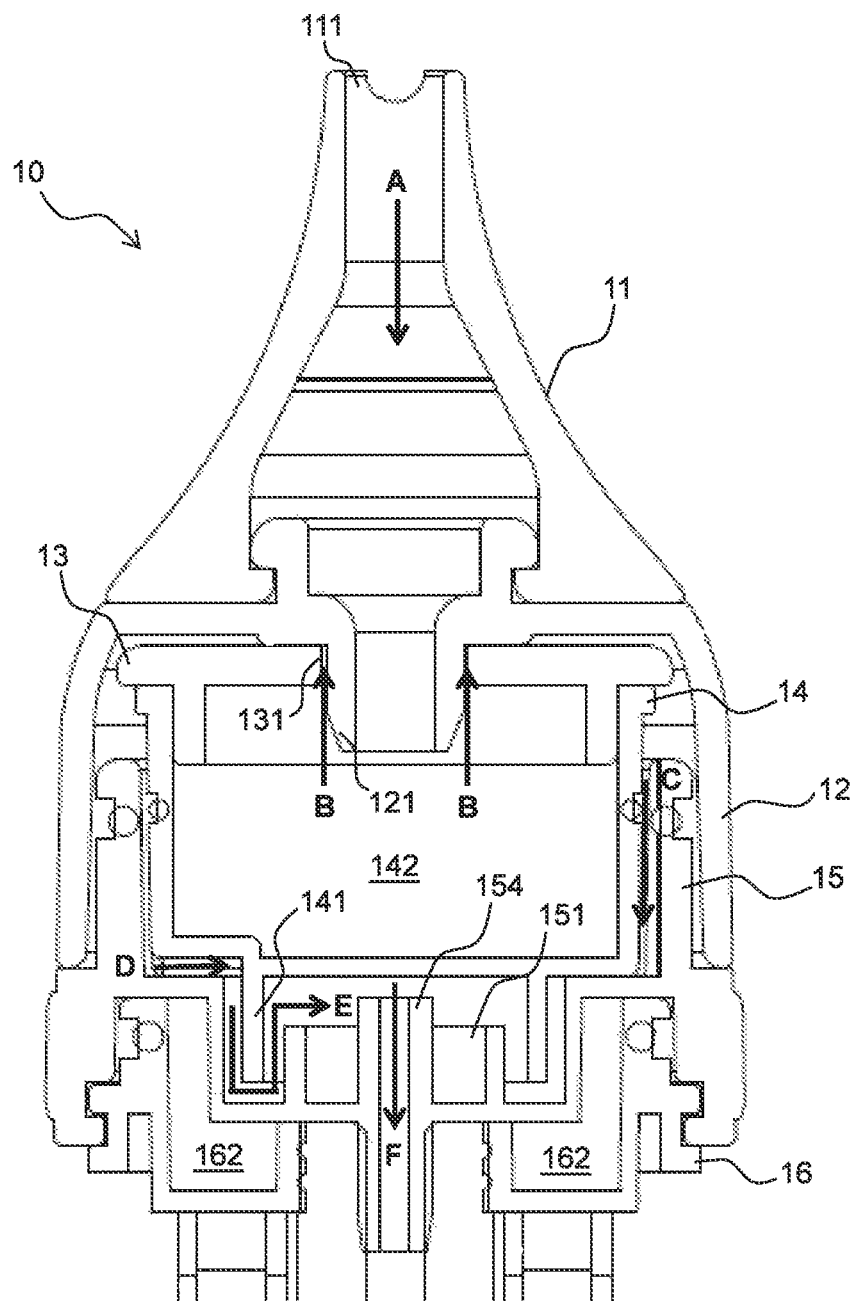
Figure 4:
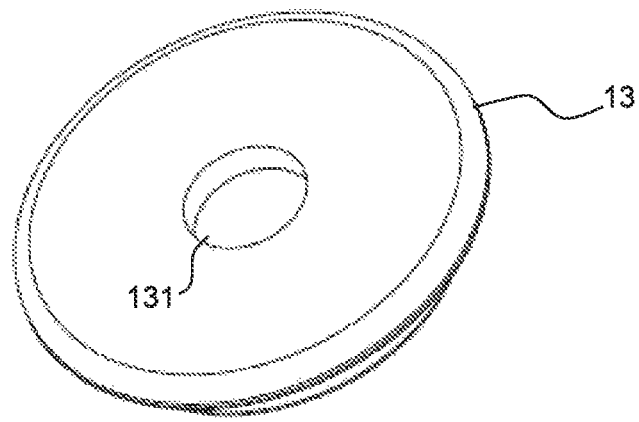
FIG. 4 is a perspective view of a cup lid of a nasal mucus suction device of the present invention.

Please refer to FIG. 3, which shows a sectional view of a head structure of a nasal mucus suction device of the present invention, and FIG. 3 is taken along section line AA of FIG. 5. In an embodiment, the front cover 11 includes a hollow channel in a trumpet shape, and is coupled to the cup cover 12. The nasal mucus suction inlet 111 is in communication with the hollow channel of the front cover 11. The cup cover 12 includes a flow guidance tube 121. As shown in FIG. 4, the cup lid 13 includes an opening 131, an internal diameter of the opening 131 is slightly greater than an outer diameter of the flow guidance tube 121, so that the nasal mucus stored in the first mucus storage cavity 142 can overflow to a space between the inner cup 14 and the cup cover 12 through an edge of the opening 131 (such as the path B). The cup lid 13 has a protruding edge structure formed on a lower surface thereof and near a periphery thereof, and the protruding edge structure is used to make the cup lid 13 tightly cover the cup edge of the inner cup 14. The flow guidance tube 121 of the cup cover 12 is inserted into the first mucus storage cavity 142 of the inner cup 14 through the opening 131 of the cup lid 13, so that the nasal mucus from the nasal mucus suction inlet 111 is stored in the first mucus storage cavity 142 of the inner cup 14 through the flow guidance tube 121.

Please refer to FIG. 5, which shows a perspective view of the outer cup 15 of the nasal mucus suction device of the present invention. As shown in FIG. 3, the outer cup 15 includes a second mucus storage cavity 153, the second mucus storage cavity 153 has a protruding edge 155 formed on an inner sidewall thereof, the protruding edge 155 is configured to support a bottom periphery of the inner cup 14. The second mucus storage cavity 153 has a middle tube 154 formed on a central part of a bottom (the space below the protruding edge 155) thereof, and an inner channel length of the middle tube 154 is greater than a bottom thickness of the outer cup 15. A lower ring wall 151 is extended from the bottom of the second mucus storage cavity 153 to surround the middle tube 154, and a height of the lower ring wall 151 is lower than a height of the middle tube 154. The inner cup 14 includes an upper ring wall 141 extended from a bottom of an outer side thereof. When the inner cup 14 is disposed inside the outer cup 15 and the protruding edge 155 supports the bottom periphery of the inner cup 14, the upper ring wall 141 surrounds the lower ring wall 151 of the outer cup 15, and the upper ring wall 141 and the lower ring wall 151 form a plurality of curved paths E of the first channel section inside the second mucus storage cavity 153 (as shown in FIG. 3), so that a path length of the first channel section can be maximized. Furthermore, the inner side of the cup cover 12 is downwardly extended to cover a part of the outer side of the outer cup 15, and the O-shaped ring 1 disposed between the outer side of the outer cup 15 and the inner side of the cup cover 12 prevents the nasal mucus overflowing the first mucus storage cavity 142 from flowing to outside the cup cover 12.

Figure 6:
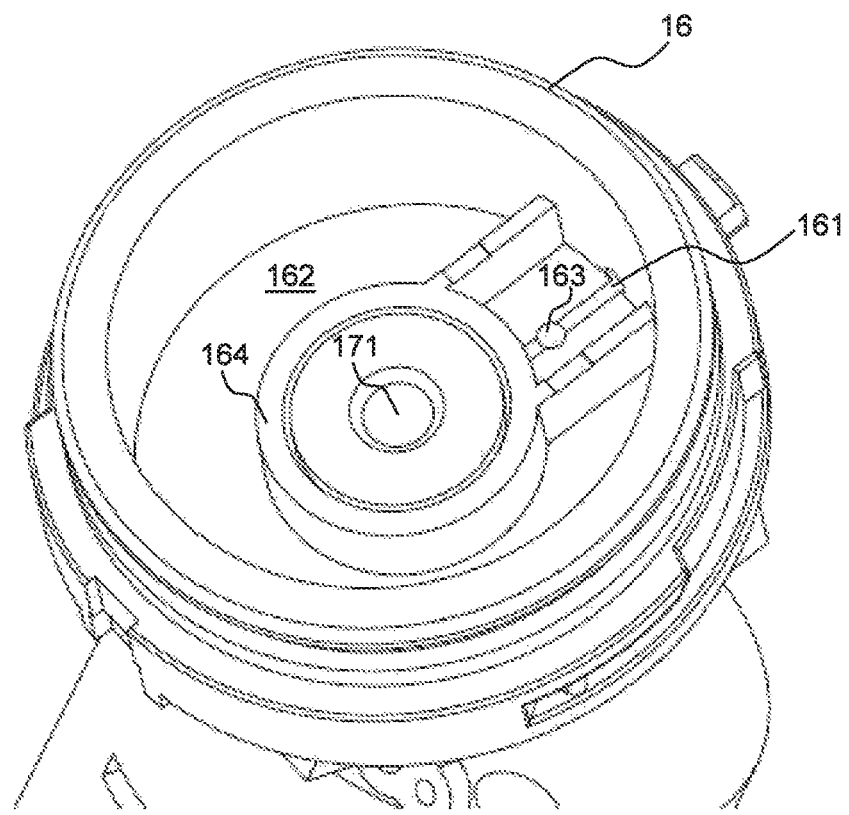
FIG. 6 is a perspective view of a base of a nasal mucus suction device of the present invention.

Please refer to FIG. 6, which shows a perspective view of a base 16 of a nasal mucus suction device of the present invention. As shown in FIGS. 2 and 6, the base 16 includes an annular inner wall 164; the annular inner wall 164 defines a channel in a central part of the base 16, and the channel is configured to link the intake channel 171 of the connection block 17. When the base 16 is coupled to the bottom of the outer cup 15, the bottom surface of the outer cup 15 is supported by the annular inner wall 164, and the middle tube 154 on the bottom of the outer cup 15 is inserted into the intake channel 171 of the connection block 17. Furthermore, the annular inner wall 164 defines an annular noise reduction space 162 inside the base 16, and an outlet chamber having a gas outlet 161. The outlet chamber includes a hole 163 in communication with the outlet channel 172 of the connection block 17. As shown in FIG. 6, the noise reduction space 162 and the outlet chamber are spaced by two partition plates, the two partition plates form a small groove, so that the noise entering the outlet chamber through the hole 163 is circulated to the noise reduction space 162 with air through the small groove, thereby achieving the effect of reducing noise. The O-shaped ring 1 disposed between the outer edge of the base 16 and the outer cup 15 can be made by rubber, so as to effectively isolate the noise of the air pump 20 inside the noise reduction space 162, thereby optimizing the noise reduction effect of the nasal mucus suction device of the present invention.

As shown in FIG. 2, the connection block 17 is coupled between the bottom of the base 16 and the air pump 20, and the connection block 17 forms an intake channel 171 and an outlet channel 172 independent from each other. The intake channel 171 is in communication with the middle tube 154 of the outer cup 15 and the intake tube 22 of the air pump 20, and the outlet channel 172 is in communication with the hole 163 of the base 16 and the outlet tube 21 of the air pump 20. In other words, the connection block 17 is used to make the intake tube 22 of the air pump 20 in communication with the second mucus storage cavity 153 of the outer cup 15, and make the outlet tube 21 of the air pump 20 in communication with the noise reduction space 162 of the base 16. The following paragraphs describe the maximization of the path length of the first channel section between the nasal mucus suction inlet 111 and the gas outlet 161 to provide prevent the nasal mucus from backflow and overflow, and describe the noise reduction space 162 of the second channel section to reduce noise caused by operation of the air pump 20.

Please refer to FIG. 3, which shows a sectional view taken along a section line AA of FIG. 5. In an embodiment of the present invention, the first channel section of the head structure 10 includes the paths A, B, C, D and E, and includes the first mucus storage cavity 142 passing through the inner cup 14 and the second mucus storage cavity 153 passing through the outer cup 15. The channel between the nasal mucus suction inlet 111 and the gas outlet 161 provide a common channel for the air channel and the nasal mucus channel. The middle tube 154 of the outer cup 15 is in communication with the intake tube 22 of the air pump 20, and when a suction force is generated in the path F, the nasal mucus from the nasal mucus suction inlet 111 can stay in the first mucus storage cavity 142 and the second mucus storage cavity 153 along the paths A, B, C, D and E. As shown in FIG. 5, a groove 152 is formed on an inner sidewall of the outer cup 15, and the section line AA passes through the groove 152. The groove 152 provides an overflowing path C for nasal mucus not restricted by the O-shaped ring 1 between the outer sidewall of the inner cup 14 and the inner sidewall of the outer cup 15. With the restriction of the O-shaped ring 1 disposed on the outer sidewall of the inner cup 14, the nasal mucus overflowing through the path B from the first mucus storage cavity 142 only can flow into between the outer sidewall of the inner cup 14 and the inner sidewall of the outer cup 15 through the path C of the groove 152.

Please refer to FIG. 3. The inner cup 14 has a groove formed on the bottom thereof to provide a path D, so that the nasal mucus between the outer sidewall of the inner cup 14 and the inner sidewall of the outer cup 15 flows into the second mucus storage cavity 153 under the inner cup 14 through the path D. More particularly, the groove of the path D is disposed opposite to the groove 152 of the outer cup 15, so that the path length of the first channel section can be maximized. When the nasal mucus passing through the path D flows into the second mucus storage cavity 153, the plurality of curved paths E formed by the upper ring wall 141 of the inner cup 14 and the lower ring wall 151 of the outer cup 15 in the second mucus storage cavity 153 can maximize the path length of the first channel section for flowing nasal mucus. Maximizing the path length of the first channel section can prevent the nasal mucus stored in the second mucus storage cavity 153 from backflowing to the nasal mucus suction inlet 111 when the air pump 20 of the nasal mucus suction device of the present invention is not in operation. In the second mucus storage cavity 153, the height of the lower ring wall 151 is lower than the height of the middle tube 154, so that the nasal mucus stored in the second mucus storage cavity 153 is prevented from flowing into the second channel section; furthermore, the middle tube 154 disposed on the central part can deflect the angle of holding the nasal mucus suction device, to prevent the nasal mucus stored in the second mucus storage cavity 153 from flowing to the second channel section easily.

Please refer to FIG. 2, which is a sectional view taken along a section line BB of FIG. 5. The section line BB is perpendicular to the section line AA, and FIGS. 2 and 3 show different sectional views of the head structure 10. In an embodiment of the present invention, the second channel section of the head structure 10 includes the paths F, G, H, I and J, and the noise reduction space 162 of the base 16. The second channel section is extended from the air channel of the first channel section to the gas outlet 161. The intake tube 22 and the outlet tube 21 of the air pump 20 pass through the intake channel 171 and the outlet channel 172 of the connection block 17 to be in communication with the middle tube 154 of the outer cup 15 and the hole 163 of the base 16, respectively. When the air pump 20 is in operation, the intake tube 22 of the air pump 20 generates a suction force in the paths F and G, and exhaust through the outlet tube 21 to the noise reduction space 162 and the gas outlet 161. Therefore, the noise generated by operation of the air pump 20 stays in the noise reduction space 162 through the paths H and I.

The present invention disclosed herein has been described by means of specific embodiments. However, numerous modifications, variations and enhancements can be made thereto by those skilled in the art without departing from the spirit and scope of the disclosure set forth in the claims.

What is claimed is:

1. A nasal mucus suction device for preventing backflow, comprising: an air pump comprising an intake tube and an outlet tube; and a head structure coupled to the intake tube and the outlet tube of the air pump, wherein the head structure has a nasal mucus suction inlet, a gas outlet and a channel defined between the nasal mucus suction inlet and the gas outlet, wherein the channel has a first channel section in communication with the nasal mucus suction inlet and a second channel section in communication with the gas outlet, wherein the first channel section has at least one mucus storage cavity and the second channel section is in communication with the intake tube and the outlet tube of the air pump, wherein the first channel section has an air channel and a nasal mucus channel and the second channel section is extended from the air channel to the gas outlet, wherein the second channel section has a noise reduction space being in communication with the outlet tube of the air pump; wherein the at least one mucus storage cavity comprises a first mucus storage cavity and a second mucus storage cavity; wherein the first channel section of the head structure comprises an inner cup, an outer cup, a cup lid, and a cup cover: wherein the inner cup has the first mucus storage cavity, which is in communication with the nasal mucus suction inlet; wherein the outer cup has the second mucus storage cavity, which is in communication with the intake tube of the air pump, and accommodates at least one part of the inner cup, so that nasal mucus overflowing from the first mucus storage cavity is accommodated in the second mucus storage cavity; wherein the cup lid has an opening and covers a cup edge of the inner cup; wherein the cup cover has a flow guidance tube and is coupled to the cup lid, so that while the flow guidance tube passes through the opening of the cup lid, the flow guidance tube guides nasal mucus from the nasal mucus suction inlet to flow into the first mucus storage cavity; wherein the flow guidance tube of the cup cover passing through the opening of the cup lid leaves a gap between the flow guidance tube and the cup lid, and another gap is formed between the inner cup and the outer cup; wherein the first channel section is arranged in a manner that, before flowing into the second mucus storage cavity, nasal mucus overflowing from the first mucus storage cavity flows through the gap between the flow guidance tube and the cup lid first, and then flows through the another gap between the inner cup and the outer cup.

2. The nasal mucus suction device according to claim 1, wherein the first channel section of the head structure comprises:

a front cover having the nasal mucus suction inlet.

3. The nasal mucus suction device according to claim 2, wherein the outer cup comprises a middle tube formed at a bottom thereof and in communication with the intake tube of the air pump and the second mucus storage cavity, wherein an inner channel length of the middle tube is greater than a bottom thickness of the outer cup.

4. The nasal mucus suction device according to claim 3, wherein the outer cup comprises a lower ring wall extended from a bottom of an inner side thereof and surrounding the middle tube, and the inner cup comprises an upper ring wall extended from a bottom of an outer side thereof and surrounding a lower ring wall of the outer cup, wherein the upper ring wall and the lower ring wall form a plurality of curved paths of the first channel section inside the second mucus storage cavity.

5. The nasal mucus suction device according to claim 2, wherein the cup cover is coupled between the front cover and the cup lid.

6. The nasal mucus suction device according to claim 1, wherein a connection block is provided in the second channel section of the head structure, wherein the connection block has an intake channel being in communication with the second mucus storage cavity of the outer cup and the intake tube of the air pump, and an outlet channel being in communication with the outlet tube and the gas outlet of the air pump.

7. The nasal mucus suction device according to claim 1, wherein the head structure further comprises a base at the second channel section, wherein the base defines a noise reduction space communicating with the gas outlet.

8. The nasal mucus suction device according to claim 7, wherein the head structure further comprises a connection block at the second channel section, wherein the connection block has an intake channel being in communication with the first channel section and the intake tube of the air pump, and an outlet channel being in communication with the outlet tube and the gas outlet of the air pump.

9. A channel forming method for a nasal mucus suction device for preventing backflow which comprises an air pump and a head structure, wherein the air pump comprises an intake tube and an outlet tube, and the head structure has a channel defined between a nasal mucus suction inlet and a gas outlet, wherein the channel has a first channel section in communication with the nasal mucus suction inlet and a second channel section in communication with the gas outlet, wherein the channel forming method comprises: disposing at least one mucus storage cavity in the first channel section, wherein the at least one mucus storage cavity comprises a first mucus storage cavity and a second mucus storage cavity; and disposing a noise reduction space in the second channel section and in communication with the outlet tube of the air pump; disposing an inner cup in the first channel section, wherein the inner cup has the first mucus storage cavity, which is in communication with the nasal mucus suction inlet; disposing an outer cup in the first channel section, wherein the outer cup has the second mucus storage cavity, which in communication with the intake tube of the air pump and configured to accommodate at least one part of the inner cup, so that the nasal mucus overflowing from the first mucus storage cavity is accommodated in the second mucus storage cavity; disposing a cup lid having an opening and covering a cup edge of the inner cup; and disposing a cup cover having a flow guidance tube that is coupled to the cup lid, so that while the flow guidance tube passes through the opening of the cup lid, the flow guidance tube guides nasal mucus from the nasal mucus suction inlet to flow into the first mucus storage cavity; wherein the first channel section is arranged in a manner that, before flowing into the second mucus storage cavity, nasal mucus overflowing from the first mucus storage cavity flows through the gap between the flow guidance tube and the cup lid first, and then flows through the another gap between the inner cup and the outer cup.

10. The channel forming method according to claim 9, further comprising:
disposing a front cover in the first channel section, wherein the front cover has a nasal mucus suction inlet.

11. The channel forming method according to claim 10, further comprising:
forming a plurality of curved paths of the first channel section in the second mucus storage cavity between an outer side bottom of the inner cup and an inner side bottom of the outer cup.

12. The channel forming method according to claim 9, further comprising:
disposing a base in the second channel section to define the noise reduction space in communication with the gas outlet.

13. The channel forming method according to claim 12, further comprising:
disposing a connection block in the second channel section, wherein the connection block has an intake channel being in communication with the first channel section and the intake tube of the air pump, and an outlet channel being in communication with the outlet tube and the gas outlet of the air pump.

* * * * *